United States Patent
Dollar et al.

(10) Patent No.: US 10,874,865 B2
(45) Date of Patent: Dec. 29, 2020

(54) EMI FEEDTHROUGH FILTER TERMINAL ASSEMBLY CONTAINING A RESIN COATING OVER A HERMETICALLY SEALING MATERIAL

(71) Applicant: AVX Corporation, Fountain Inn, SC (US)

(72) Inventors: Don Dollar, Fountain Inn, SC (US); Rigoberto Rios, Fountain Inn, SC (US)

(73) Assignee: AVX Corporation, Fountain Inn, SC (US)

( * ) Notice: Subject to any disclaimer, the term of this patent is extended or adjusted under 35 U.S.C. 154(b) by 59 days.

(21) Appl. No.: 16/181,662

(22) Filed: Nov. 6, 2018

(65) Prior Publication Data

US 2019/0134407 A1    May 9, 2019

Related U.S. Application Data

(60) Provisional application No. 62/582,028, filed on Nov. 6, 2017, provisional application No. 62/582,040, filed on Nov. 6, 2017.

(51) Int. Cl.
*A61N 1/375* (2006.01)
*H01G 4/35* (2006.01)
(Continued)

(52) U.S. Cl.
CPC ........... *A61N 1/3754* (2013.01); *H01G 4/224* (2013.01); *H01G 4/236* (2013.01); *H01G 4/35* (2013.01);
(Continued)

(58) Field of Classification Search
CPC ................................ A61N 1/3754; A61N 4/35
See application file for complete search history.

(56) References Cited

U.S. PATENT DOCUMENTS

| 1,180,614 A | 4/1916 | Otto |
| 2,756,375 A | 7/1956 | Peck |
| (Continued) | | |

FOREIGN PATENT DOCUMENTS

| DE | 2815118 | 10/1978 |
| EP | 0331959 | 9/1989 |

OTHER PUBLICATIONS

International Search Report for PCT/US2018/059369 dated Feb. 26, 2019, 21 pages.

*Primary Examiner* — Eric W Thomas
(74) *Attorney, Agent, or Firm* — Dority & Manning, P.A.

(57) ABSTRACT

The present invention is directed to an EMI feedthrough filter terminal assembly. The EMI feedthrough filter terminal assembly comprises: a feedthrough filter capacitor having a plurality of first electrode layers and a plurality of second electrode layers and a first passageway therethrough having a first termination surface conductively coupling the plurality of first electrode layers; at least one conductive terminal pin extending through the passageway in conductive relation with the plurality of first electrode layers; a feedthrough ferrule; an insulator fixed to the feedthrough ferrule for conductively isolating the conductive terminal pin from the feedthrough ferrule; a hermetically sealing material between the insulator and the feedthrough ferrule; and a resin coating over the hermetically sealing material.

17 Claims, 4 Drawing Sheets

(51) Int. Cl.
  *H01G 4/236* (2006.01)
  *H01H 1/00* (2006.01)
  *H01G 4/224* (2006.01)
  *H03H 1/00* (2006.01)

(52) U.S. Cl.
  CPC ... *H03H 1/0007* (2013.01); *H03H 2001/0014* (2013.01); *H03H 2001/0042* (2013.01)

(56) References Cited

U.S. PATENT DOCUMENTS

| | | |
|---|---|---|
| 3,235,939 A | 2/1966 | Rodriguez et al. |
| 3,266,121 A | 8/1966 | Rayburn |
| 3,304,362 A | 2/1967 | August |
| 3,538,464 A | 11/1970 | Walsh |
| 3,624,460 A | 11/1971 | Correll |
| 3,844,921 A | 10/1974 | Benedict |
| 3,920,888 A | 11/1975 | Barr |
| 4,010,759 A | 3/1977 | Boer |
| 4,015,175 A | 3/1977 | Kendall et al. |
| 4,041,587 A | 8/1977 | Kraus |
| 4,083,022 A | 4/1978 | Nijman |
| 4,107,762 A | 8/1978 | Shirn et al. |
| 4,148,003 A | 4/1979 | Colburn et al. |
| 4,152,540 A | 5/1979 | Brown et al. |
| 4,168,351 A | 9/1979 | Taylor |
| 4,220,813 A | 9/1980 | Kyle |
| 4,225,262 A | 9/1980 | Koop et al. |
| 4,246,556 A | 1/1981 | Snow |
| 4,247,881 A | 1/1981 | Coleman |
| 4,262,268 A | 4/1981 | Shimada et al. |
| 4,314,213 A | 2/1982 | Wakino |
| 4,352,951 A | 10/1982 | Kyle |
| 4,362,792 A | 12/1982 | Bowsky et al. |
| 4,421,947 A | 12/1983 | Kyle |
| 4,424,551 A | 1/1984 | Stevenson et al. |
| 4,456,786 A | 6/1984 | Kyle |
| 4,556,613 A | 12/1985 | Taylor et al. |
| 4,606,598 A | 8/1986 | Drzymkowski et al. |
| 4,683,516 A | 7/1987 | Miller |
| 4,737,601 A | 4/1988 | Gartzke |
| 4,741,710 A | 5/1988 | Hogan et al. |
| 4,791,391 A | 12/1988 | Linnell et al. |
| 4,835,365 A | 5/1989 | Etheridge |
| 4,934,366 A | 6/1990 | Truex et al. |
| 5,023,147 A | 6/1991 | Nakata et al. |
| 5,032,692 A | 7/1991 | Devolder |
| 5,046,242 A | 9/1991 | Kuzma |
| 5,070,605 A | 12/1991 | Daglow et al. |
| 5,104,755 A | 4/1992 | Taylor et al. |
| 5,144,946 A | 9/1992 | Weinberg et al. |
| 5,333,095 A | 7/1994 | Stevenson et al. |
| 5,406,444 A | 4/1995 | Seifried et al. |
| 5,440,447 A | 8/1995 | Shipman et al. |
| 5,531,003 A | 7/1996 | Seifried et al. |
| 5,535,097 A | 7/1996 | Ruben et al. |
| 5,538,810 A | 7/1996 | Kaun |
| 5,620,476 A | 4/1997 | Truex et al. |
| 5,650,759 A | 7/1997 | Hittman et al. |
| 5,681,172 A | 10/1997 | Moldenhauer |
| 5,700,724 A | 12/1997 | Shipe |
| 5,735,884 A | 4/1998 | Thompson et al. |
| 5,833,714 A | 11/1998 | Loeb |
| 5,836,992 A | 11/1998 | Thompson et al. |
| 5,870,272 A | 2/1999 | Seifried et al. |
| 5,896,267 A | 4/1999 | Hittman et al. |
| 5,905,627 A | 5/1999 | Brendel et al. |
| 5,959,829 A | 9/1999 | Stevenson et al. |
| 5,973,906 A | 10/1999 | Stevenson et al. |
| 5,999,398 A | 12/1999 | Makl et al. |
| 6,008,980 A | 12/1999 | Stevenson et al. |
| 6,031,710 A | 2/2000 | Wolf et al. |
| 6,159,560 A | 12/2000 | Stevenson et al. |
| 6,275,369 B1 | 8/2001 | Stevenson et al. |
| 6,324,047 B1 | 11/2001 | Hayworth |
| 6,349,025 B1 | 2/2002 | Fraley et al. |
| 6,424,234 B1 | 7/2002 | Stevenson |
| 6,456,481 B1 | 9/2002 | Stevenson |
| 6,459,935 B1 | 10/2002 | Piersma |
| 6,473,291 B1 | 10/2002 | Stevenson |
| 6,490,148 B1 | 12/2002 | Allen et al. |
| 6,529,103 B1 | 3/2003 | Brendel et al. |
| 6,566,978 B2 | 5/2003 | Stevenson et al. |
| 6,586,675 B1 | 7/2003 | Bealka et al. |
| 6,610,443 B2 | 8/2003 | Paulot et al. |
| 6,626,680 B2 | 9/2003 | Ciurzynski et al. |
| 6,643,903 B2 | 11/2003 | Stevenson et al. |
| 6,765,779 B2 | 7/2004 | Stevenson et al. |
| 6,765,780 B2 | 7/2004 | Brendel et al. |
| 6,768,629 B1 | 7/2004 | Allen et al. |
| 6,781,088 B2 | 8/2004 | Grubb et al. |
| 6,857,915 B2 | 2/2005 | Ciurzynski et al. |
| 6,882,248 B2 | 4/2005 | Stevenson et al. |
| 6,888,715 B2 | 5/2005 | Stevenson et al. |
| 6,920,673 B2 | 7/2005 | Allen et al. |
| 6,985,347 B2 | 1/2006 | Stevenson et al. |
| 6,987,660 B2 | 1/2006 | Stevenson et al. |
| 6,999,818 B2 | 2/2006 | Stevenson et al. |
| 7,012,192 B2 | 3/2006 | Stevenson et al. |
| 7,035,076 B1 | 4/2006 | Stevenson |
| 7,035,077 B2 | 4/2006 | Brendel |
| 7,038,900 B2 | 5/2006 | Stevenson et al. |
| 7,079,903 B2 | 7/2006 | O'Brien |
| 7,113,387 B2 | 9/2006 | Stevenson et al. |
| 7,128,765 B2 | 10/2006 | Paulot et al. |
| 7,136,273 B2 | 11/2006 | Stevenson et al. |
| 7,145,076 B2 | 12/2006 | Knappen et al. |
| 7,162,308 B2 | 1/2007 | O'Brien et al. |
| 7,186,049 B1 | 3/2007 | Grubb et al. |
| 7,199,995 B2 | 4/2007 | Stevenson |
| 7,310,216 B2 | 12/2007 | Stevenson et al. |
| 7,327,553 B2 | 2/2008 | Brendel |
| 7,489,495 B2 | 2/2009 | Stevenson |
| 7,535,693 B2 | 5/2009 | Stevenson et al. |
| 7,551,963 B2 | 6/2009 | Rusin et al. |
| 7,564,674 B2 | 7/2009 | Frysz et al. |
| 7,569,452 B2 | 8/2009 | Fu et al. |
| 7,623,335 B2 | 11/2009 | Stevenson et al. |
| 7,623,336 B2 | 11/2009 | Stevenson et al. |
| 7,702,387 B2 | 4/2010 | Stevenson et al. |
| 7,751,903 B2 | 7/2010 | Stevenson et al. |
| 7,765,005 B2 | 7/2010 | Stevenson |
| 7,797,048 B2 | 9/2010 | Stevenson et al. |
| 7,804,676 B2 | 9/2010 | Brendel et al. |
| 7,812,691 B1 | 10/2010 | Fisk et al. |
| 7,844,319 B2 | 11/2010 | Susil et al. |
| 7,853,324 B2 | 12/2010 | Stevenson et al. |
| 7,853,325 B2 | 12/2010 | Dabney et al. |
| 7,899,551 B2 | 3/2011 | Westlund et al. |
| 7,917,219 B2 | 3/2011 | Stevenson et al. |
| 7,920,916 B2 | 4/2011 | Johnson et al. |
| 7,945,322 B2 | 5/2011 | Stevenson et al. |
| 7,957,806 B2 | 6/2011 | Stevenson et al. |
| 7,966,075 B2 | 6/2011 | Johnson et al. |
| 8,000,801 B2 | 8/2011 | Stevenson et al. |
| 8,065,009 B2 | 11/2011 | Biggs |
| 8,095,224 B2 | 1/2012 | Truex et al. |
| 8,108,042 B1 | 1/2012 | Johnson et al. |
| 8,116,862 B2 | 2/2012 | Stevenson et al. |
| 8,145,324 B1 | 3/2012 | Stevenson et al. |
| 8,155,760 B2 | 4/2012 | Westlund et al. |
| 8,175,700 B2 | 5/2012 | Johnson et al. |
| 8,179,658 B2 | 5/2012 | Brendel et al. |
| 8,180,448 B2 | 5/2012 | Stevenson et al. |
| 8,195,295 B2 | 6/2012 | Stevenson et al. |
| 8,200,328 B2 | 6/2012 | Stevenson et al. |
| 8,200,342 B2 | 6/2012 | Stevenson et al. |
| 8,219,208 B2 | 7/2012 | Stevenson et al. |
| 8,224,440 B2 | 7/2012 | Bauer et al. |
| 8,224,462 B2 | 7/2012 | Westlund et al. |
| 8,239,041 B2 | 8/2012 | Kondabatni et al. |
| 8,244,370 B2 | 8/2012 | Halperin et al. |
| 8,275,466 B2 | 9/2012 | Halperin et al. |
| 8,301,243 B2 | 10/2012 | Stevenson et al. |

(56) References Cited

U.S. PATENT DOCUMENTS

| | | |
|---|---|---|
| 8,311,628 B2 | 11/2012 | Stevenson et al. |
| 8,321,032 B2 | 11/2012 | Frysz et al. |
| 8,331,077 B2 | 12/2012 | Iyer |
| 8,346,362 B2 | 1/2013 | Kinney et al. |
| 8,364,283 B2 | 1/2013 | Halperin et al. |
| 8,369,951 B2 | 2/2013 | Smith et al. |
| 8,422,195 B2 | 4/2013 | Stevenson |
| 8,433,410 B2 | 4/2013 | Stevenson et al. |
| 8,437,865 B2 | 5/2013 | Dabney et al. |
| 8,447,414 B2 | 5/2013 | Johnson et al. |
| 8,457,760 B2 | 6/2013 | Johnson et al. |
| 8,463,375 B2 | 6/2013 | Stevenson et al. |
| 8,468,664 B2 | 6/2013 | Brendel et al. |
| 8,483,840 B2 | 7/2013 | Stevenson et al. |
| 8,494,636 B2 | 7/2013 | Smith et al. |
| 8,509,913 B2 | 8/2013 | Johnson et al. |
| 8,577,453 B1 | 11/2013 | Stevenson et al. |
| 8,600,519 B2 | 12/2013 | Stevenson et al. |
| 8,642,887 B1 | 2/2014 | Li et al. |
| 8,648,255 B2 | 2/2014 | Talamine et al. |
| 8,648,265 B2 | 2/2014 | Talamine et al. |
| 8,649,857 B2 | 2/2014 | Stevenson et al. |
| 8,653,384 B2 | 2/2014 | Tang et al. |
| 8,659,870 B2 | 2/2014 | Brendel et al. |
| 8,660,645 B2 | 2/2014 | Stevenson et al. |
| 8,670,841 B2 | 3/2014 | Dabney et al. |
| 8,712,544 B2 | 4/2014 | Dabney et al. |
| 8,722,238 B2 | 5/2014 | Dai |
| 8,751,013 B2 | 6/2014 | Johnson et al. |
| 8,761,895 B2 | 6/2014 | Stevenson et al. |
| 8,849,403 B2 | 9/2014 | Johnson et al. |
| 8,855,768 B1 | 10/2014 | Johnson et al. |
| 8,855,785 B1 | 10/2014 | Johnson et al. |
| 8,868,189 B2 | 10/2014 | Stevenson et al. |
| 8,897,887 B2 | 11/2014 | Halperin et al. |
| 8,903,505 B2 | 12/2014 | Stevenson et al. |
| 8,918,189 B2 | 12/2014 | Dabney et al. |
| 8,938,309 B2 | 1/2015 | Marzano et al. |
| 8,977,355 B2 | 3/2015 | Stevenson et al. |
| 8,989,870 B2 | 3/2015 | Johnson et al. |
| 8,996,126 B2 | 3/2015 | Stevenson et al. |
| 9,008,799 B2 | 4/2015 | Stevenson et al. |
| 9,014,808 B2 | 4/2015 | Stevenson et al. |
| 9,031,670 B2 | 5/2015 | Dabney et al. |
| 9,037,258 B2 | 5/2015 | Johnson et al. |
| 9,042,999 B2 | 5/2015 | Stevenson et al. |
| 9,061,139 B2 | 6/2015 | Stevenson et al. |
| 9,064,640 B2 | 6/2015 | Brendel et al. |
| 9,065,224 B2 | 6/2015 | Marzano et al. |
| 9,071,221 B1 | 6/2015 | Stevenson et al. |
| 9,093,974 B2 | 7/2015 | Ritter et al. |
| 9,108,066 B2 | 8/2015 | Woods et al. |
| 9,119,968 B2 | 9/2015 | Halperin et al. |
| 9,233,253 B2 | 1/2016 | Stevenson et al. |
| 9,248,283 B2 | 2/2016 | Halperin et al. |
| 9,251,960 B2 | 2/2016 | Brendel et al. |
| 9,254,377 B2 | 2/2016 | Kondabatni et al. |
| 9,352,150 B2 | 5/2016 | Stevenson et al. |
| 9,427,596 B2 | 8/2016 | Woods et al. |
| 9,463,329 B2 | 10/2016 | Frysz et al. |
| 9,492,659 B2 | 11/2016 | Tang et al. |
| 9,511,220 B2 | 12/2016 | Marzano et al. |
| 9,692,173 B2 | 6/2017 | Marzano et al. |
| 9,757,558 B2 | 9/2017 | Stevenson et al. |
| 9,764,129 B2 | 9/2017 | Stevenson et al. |
| 2003/0081370 A1 | 5/2003 | Haskell et al. |
| 2003/0213605 A1* | 11/2003 | Brendel ............... A61N 1/3754 174/360 |
| 2007/0043399 A1* | 2/2007 | Stevenson ........... A61N 1/3754 607/37 |
| 2008/0033496 A1 | 2/2008 | Iyer et al. |
| 2009/0059468 A1* | 3/2009 | Iyer .................... A61N 1/3754 361/302 |
| 2013/0286537 A1 | 10/2013 | Brendel et al. |
| 2014/0168917 A1 | 6/2014 | Marzano et al. |
| 2014/0194964 A1 | 7/2014 | Woods et al. |
| 2014/0240060 A1 | 8/2014 | Stevenson et al. |
| 2014/0245600 A1 | 9/2014 | Dai |
| 2014/0246408 A1 | 9/2014 | Dai |
| 2014/0330355 A1 | 11/2014 | Stevenson et al. |
| 2015/0066124 A1 | 3/2015 | Stevenson et al. |
| 2015/0282391 A1 | 10/2015 | Ritter et al. |
| 2015/0314131 A1 | 11/2015 | Stevenson et al. |
| 2016/0263373 A1 | 9/2016 | Stevenson et al. |
| 2016/0263384 A1 | 9/2016 | Stevenson et al. |
| 2016/0346555 A1 | 12/2016 | Ritter |
| 2016/0367821 A1 | 12/2016 | Frysz et al. |
| 2017/0080239 A1 | 3/2017 | Seitz et al. |
| 2017/0087354 A1 | 3/2017 | Stevenson et al. |
| 2017/0087355 A1 | 3/2017 | Stevenson et al. |
| 2017/0087356 A1 | 3/2017 | Stevenson et al. |
| 2017/0117866 A1 | 4/2017 | Stevenson et al. |

* cited by examiner

EMI FEEDTHROUGH FILTER TERMINAL ASSEMBLY CONTAINING A RESIN COATING OVER A HERMETICALLY SEALING MATERIAL

CROSS-REFERENCE TO RELATED APPLICATION

The present application claims filing benefit of U.S. Provisional Patent Application Ser. Nos. 62/582,028 and 62/582,040 both having a filing date of Nov. 6, 2017 and which are incorporated herein by reference in their entirety.

BACKGROUND OF THE INVENTION

Feedthrough filter assemblies are generally well known in the art for connecting electrical signals through the housing of an electronic instrument. Typically, the terminal pin assembly comprises one or more conductive terminal pins supported by an insulator structure for feedthrough passage from the exterior to the interior of a medical device. Because it is desired to prevent the entry of body fluids into the housing of the medical device, it is desired to provide an insulator structure and mounting method that provide a hermetic seal. Additionally, the hermetic terminal pin subassembly has been combined in various ways with a ceramic feedthrough filter capacitor to decouple interference signals to the housing of the medical device.

While the prior art has provided various configurations for EMI feedthrough filter assemblies, there is nevertheless a need for an improved configuration.

SUMMARY OF THE INVENTION

In accordance with one embodiment of the present invention, an EMI feedthrough filter terminal assembly is disclosed. The EMI feedthrough filter terminal assembly comprises: a feedthrough filter capacitor having a plurality of first electrode layers and a plurality of second electrode layers and a first passageway therethrough having a first termination surface conductively coupling the plurality of first electrode layers; at least one conductive terminal pin extending through the passageway in conductive relation with the plurality of first electrode layers; a feedthrough ferrule; an insulator fixed to the feedthrough ferrule for conductively isolating the conductive terminal pin from the feedthrough ferrule; a hermetically sealing material between the insulator and the feedthrough ferrule; and a resin coating over the hermetically sealing material.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
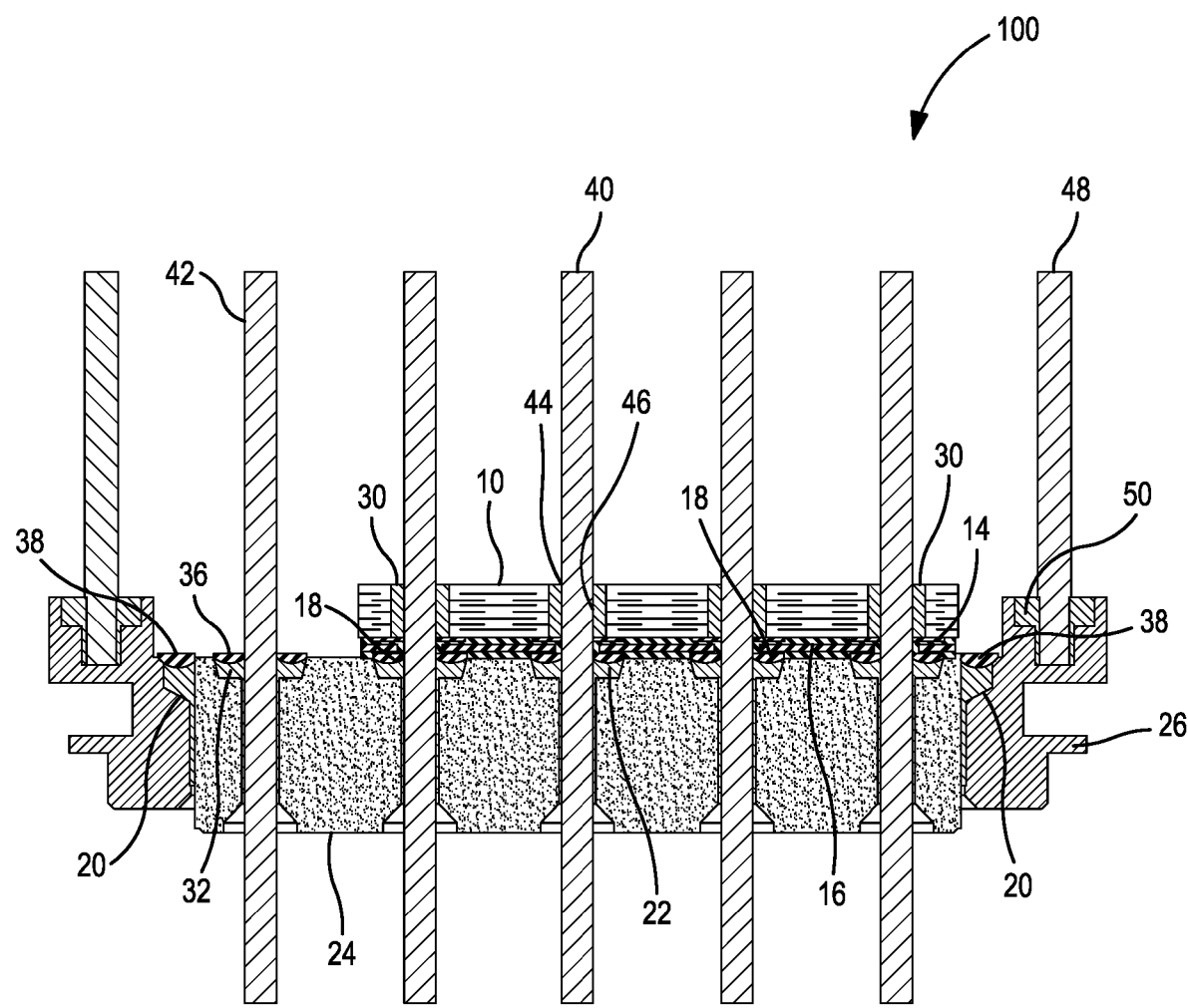
FIG. 1 illustrates a front cross-sectional view of one embodiment of a feedthrough filter assembly according to the present invention.

It is to be understood by one of ordinary skill in the art that the present discussion is a description of exemplary embodiments only, and is not intended as limiting the broader aspects of the present invention.

Generally speaking, the present invention is directed to an EMI feedthrough filter terminal assembly. In particular, the present invention is directed to an EMI feedthrough filter terminal assembly that employs a resin coating over a hermetically sealing material. The present inventors have discovered that such a resin coating can provide an EMI feedthrough filter terminal assembly with improved benefits and/or performance.

For instance, the capacitor may have a capacitance range of about 1000 pF or more, such as about 1300 pf or more, such as about 1500 pf or more, such as about 1700 pf or more to about 3000 pf or less, such as about 2500 pf or less, such as about 2200 pf or less, such as about 2000 pf or less at 1 KHz. At 1 MHz, the capacitor may have a minimum of at least 500 pf, such as at least 700 pf, such as at least 900 pf, such as at least 1000 pf. In addition, the capacitor may have a low parasitic capacitor. For instance, the capacitor may have a parasitic capacitance of about 30 pf or less, such as about 25 pf or less, such as about 20 pf or less, such as 15 pf or less, such as about 10 pf or less, such as about 5 pf or less. Furthermore, the capacitor has a low ESR of about 25 Ohms or less, such as about 20 Ohms or less, such as about 10 Ohms or less, such as about 5 Ohms or less, such as about 3 Ohms or less, such as about 2 Ohms or less at 1 Mhz.

Feedthrough filter assemblies are generally well known in the art for connecting electrical signals through the housing of an electronic instrument. Broadly, the EMI feedthrough filter terminal assembly includes a feedthrough filter capacitor, a feedthrough ferrule, a conductive terminal pin, a ferrule, and an insulator. The EMI feedthrough filter terminal assembly can include a hermetic seal, which can prevent the entry of body fluids into the housing of a medical device.

As indicated, the EMI feedthrough filter terminal assembly includes a feedthrough filter capacitor. The capacitor can generally include any type of ceramic capacitor known in the art. For instance, the capacitor may be a multilayer ceramic capacitor containing a plurality of dielectric layers separating a plurality of electrode layers. Generally, the electrode layers may include a plurality of first electrode layers and a plurality of second electrode layers that are in an alternating and interleaved configuration. In one embodiment, the plurality of first electrode layers may be referred to as the active electrode layers while the plurality of second electrode layers may be referred to as the ground electrode layers. The active electrode layers may extend toward an inner diameter cylindrical surface of a passageway of the capacitor. In this regard, the plurality of first electrode layers may be conductively coupled at a first termination surface. Meanwhile, the ground electrode layers may extend toward a perimeter edge at an outer periphery of the capacitor. Such ground electrode layers may be electrically connected by a suitable conductive surface such as a surface metallization layer. In this regard, the plurality of second electrode layers may be conductively coupled at a second termination surface.

In the capacitors, any dielectric material known in the art may be used for the dielectric layers. For instance, the dielectric layers are typically formed from a material having a relatively high dielectric constant (K), such as from about 10 to about 40,000 in some embodiments from about 50 to about 30,000, and in some embodiments, from about 100 to about 20,000.

In this regard, the dielectric material may be a ceramic. The ceramic may be provided in a variety of forms, such as a wafer (e.g., pre-fired) or a dielectric material that is co-fired within the device itself.

Particular examples of the type of high dielectric material include, for instance, NPO (COG) (up to about 100), X7R (from about 3,000 to about 7,000), X7S, Z5U, and/or Y5V materials. It should be appreciated that the aforementioned materials are described by their industry-accepted definitions, some of which are standard classifications established by the Electronic Industries Alliance (EIA), and as such should be recognized by one of ordinary skill in the art. For instance, such material may include a ceramic. Such materials may include a perovskite, such as barium titanate and related solid solutions (e.g., barium-strontium titanate, barium calcium titanate, barium zirconate titanate, barium strontium zirconate titanate, barium calcium zirconate titanate, etc.), lead titanate and related solid solutions (e.g., lead zirconate titanate, lead lanthanum zirconate titanate), sodium bismuth titanate, and so forth. In one particular embodiment, for instance, barium strontium titanate ("BSTO") of the formula $Ba_xSr_{1-x}TiO_3$ may be employed, wherein x is from 0 to 1, in some embodiments from about 0.15 to about 0.65, and in some embodiments, from about from 0.25 to about 0.6. Other suitable perovskites may include, for instance, $Ba_xCa_{1-x}TiO_3$ where x is from about 0.2 to about 0.8, and in some embodiments, from about 0.4 to about 0.6, $Pb_xZr_{1-x}TiO_3$ ("PZT") where x ranges from about 0.05 to about 0.4, lead lanthanum zirconium titanate ("PLZT"), lead titanate ($PbTiO_3$), barium calcium zirconium titanate ($BaCaZrTiO_3$), sodium nitrate ($NaNO_3$), $KNbO_3$, $LiNbO_3$, $LiTaO_3$, $PbNb_2O_6$, $PbTa_2O_6$, $KSr(NbO_3)$ and $NaBa_2(NbO_3)_5KHb_2PO_4$. Still additional complex perovskites may include $A[B1_{1/3}B2_{2/3}]O_3$ materials, where A is $Ba_xSr_{1-x}$ (x can be a value from 0 to 1); B1 is $Mg_yZn_{1-y}$ (y can be a value from 0 to 1); B2 is $Ta_zNb_{1-z}$ (z can be a value from 0 to 1). In one particular embodiment, the dielectric layers may comprise a titanate.

In the capacitors, any electrode material known in the art may be employed for the electrodes. For instance, the electrode layers may be formed from any of a variety of different metals as is known in the art. The electrode layers may be made from a metal, such as a conductive metal. The materials may include precious metals (e.g., silver, gold, palladium, platinum, etc.), base metals (e.g., copper, tin, nickel, chrome, titanium, tungsten, etc.), and so forth, as well as various combinations thereof. Sputtered titanium/tungsten (Ti/W) alloys, as well as respective sputtered layers of chrome, nickel and gold, may also be suitable. The electrodes may also be made of a low resistive material, such as silver, copper, gold, aluminum, palladium, etc. In one particular embodiment, the electrode layers may comprise nickel or an alloy thereof. In another embodiment, the electrode layers may comprise silver or an alloy thereof, such as a silver palladium alloy.

The external terminals, such as the second termination surfaces, may be formed from any of a variety of different metals as known in the art. The external terminals may be made from a metal, such as a conductive metal. The materials may include precious metals (e.g., silver, gold, palladium, platinum, etc.), base metals (e.g., copper, tin, nickel, chrome, titanium, tungsten, etc.), and so forth, as well as various combinations thereof. In one particular embodiment, the external terminals may comprise copper or an alloy thereof. In another embodiment, they may comprise silver. For instance, such terminal may be formed by a silver polyimide paste that is cured.

The external terminals can be formed using any method generally known in the art. The external terminals may be formed using techniques such as sputtering, painting, printing, electroless plating or fine copper termination (FCT), electroplating, plasma deposition, propellant spray/air brushing, and so forth.

Additionally, it should be understood that the number and thicknesses of the layers, both the dielectric layer and the electrode layers, as well as the spacing between adjacent layers may vary depending on the desired capacitance value and the voltage rating of the capacitor. In addition, in one embodiment, the capacitor may be a capacitor array containing a plurality of capacitive elements.

In general, the electrodes can be conductively coupled using various techniques. These techniques may include metallization of the passageway (e.g., solder joint, braze, weld, etc.) or a thermosetting conductive polymer joint between the capacitor and the conductive terminal pin. For instance, such thermosetting conductive polymer may be a polyimide. For instance, such polyimide may include a conductive metal, such as silver for imparting conductivity. Such metallization or conductive polymer may extend axially through the feedthrough filter capacitor. In addition, such polyimide may be placed into the passageway and cured. Alternatively, such polyimide for coating the passageway may be pre-formed and inserted into the passageway to cover the inner diameter cylindrical surface.

As indicated, the EMI feedthrough filter terminal assembly includes a feedthrough ferrule. In general, the feedthrough ferrule is made from a biocompatible material, such as a biocompatible metal. For instance, the feedthrough ferrule can be made from titanium, niobium, tantalum, and the like. In one embodiment, the feedthrough ferrule can be made from titanium. For instance, the feedthrough ferrule may be a titanium-ceramic composite structure. In this regard, the feedthrough ferrule may be a conductive feedthrough ferrule.

In one embodiment, the feedthrough ferrule may be conductively coupled to the capacitor. For instance, the feedthrough ferrule may be conductively coupled to the ground electrode layers of the capacitor. Such conductive coupling may be according to any method known in the art. For instance, such coupling may be via a joint, such as a ground joint. Such joint may be a metallized joint (e.g., brazing, soldering, welding, etc.) or may be a conductive thermosetting polymer joint. For instance, such soldering may be with a solder paste that may wet and/or bond to a hermetically sealing material, such as a gold brazing. Additionally, the conductive thermosetting polymer may be a polyimide. For instance, such polyimide may include a conductive metal, such as silver for imparting conductivity.

Such coupling, in addition to being conductive, may also be mechanical. In addition, such coupling may provide a gap between a facing surface (e.g., a bottom facing surface or a top facing surface) of the capacitor, the laminated insulative layer, the coupling joint, and the insulator.

In another embodiment, the capacitor may be internally grounded. For instance, in such an embodiment, a ground pin may be employed. Such ground pin may be connected (e.g., brazed) directly to the ferrule. In another embodiment, a ground pin may be employed that does not extend through the capacitor. For instance, such ground pin may be for externally grounding the capacitor via the ferrule and second termination surface of the capacitor.

As indicated, the EMI feedthrough filter terminal assembly includes conductive terminal pins. The conductive terminal pins are electrically connected to the electrode layers of the capacitor at an inner diameter cylindrical surface of the capacitor. In addition, the conductive terminal pin may also extend through the feedthrough ferrule in a non-conductive relation. The pins may be made from any material generally known in the art. For instance, the pins may be a metal. In particular, the pins may be platinum, gold, titanium, niobium, tantalum, palladium, iridium, alloys thereof or the like. For instance, in one embodiment, the pins may be a single solid alloy material (i.e., no separate core and coatings). In particular, the pins may be a palladium/iridium alloy. For instance, the alloy may contain 75% by weight or more palladium, such as 80% by weight or more palladium, such as 85% by weight or more palladium and 25% by weight or less iridium, such as 20% by weight or less iridium, such as 15% by weight or less iridium.

It should be understood that the number of pins should not be limited. For instance, the EMI feedthrough filter terminal assembly may be unipolar (one), bipolar (two), tripolar (three), quadpolar (four), pentapolar (five), hexpolar (six), etc. In one embodiment, the EMI feedthrough filter terminal assembly may be quadpolar, including four conductive terminal pins.

In addition, in one embodiment, the EMI feedthrough filter terminal assembly includes an RF pin. For instance, the RF pin may be an RF telemetry pin as generally employed in the art. Such pin may allow a physician to use a radio frequency interrogator to interrogate a patient sitting in a chair across the room while the physician is sitting conveniently at his or her desk.

In addition to the above, the EMI feedthrough filter terminal assembly may include other pins that are not active conductive terminal pins or RF pins. For instance, such pins may be incorporated to provide mechanical stability or for providing a location for connection. In addition, as indicated above, a ground pin may be employed for internally grounding the capacitor. In addition, other ground pins may be employed that do not pass through the capacitor; for instance, such pins may pass only into the feedthrough ferrule and not through the capacitor or insulator.

As indicated, the EMI feedthrough filter terminal assembly includes an insulator. In general, the insulator can be fixed to the feedthrough ferrule. The insulator can be utilized to conductively isolate a terminal pin from the feedthrough ferrule. In this regard, the insulator may be a ceramic material, for example one having good insulating properties. For instance, the insulator may be an alumina insulator or the like. For instance, the insulator may be 99.9% alumina. Alternatively, the insulator may be glass or the like. In one particular embodiment, the insulator includes an alumina insulator.

In general, the insulator may also provide a hermetic seal against body fluids. For instance, the conductive terminal pins may be installed into the insulator using a material that provides a hermetic seal. In addition, the hermetic seal may also be formed between the insulator and the feedthrough ferrule. Further, such hermetic seal may also be formed between the insulator and an RF pin when present. Such hermetic seal can be formed from a hermetically sealing material that is present through at least 30%, such as at least 40%, such as at least 50%, such as at least 60% of the thickness of the insulator in the direction in which the conductive terminal pin extends. In addition, the width of the presence of the hermetically sealing material may be greater adjacent the insulative layer than the width at approximately a 50% thickness of the insulator.

Such hermetic seal can be provided using a hermetically sealing material as generally employed in the art. The hermetic seal may generally be formed from a noble material, such as silver, platinum, iridium, gold, and the like. In one embodiment, the hermetic seal may be formed from gold, such as a gold brazing. The gold brazing may be 99% by weight or more gold, such as 99.9% by weight or more gold, such as 99.99% by weight or more gold, such as 99.999% by weight or more gold. Aside from gold brazing, it should be understood that other materials, such as sealing glass, may also be employed for providing a hermetic seal.

In addition, the hermetic seal may also include metallization on the insulator. Such metallization may include an active layer and a barrier layer for protecting the active layer. For instance, the insulator may include a titanium/molybdenum metallization to provide a hermetic seal. For instance, titanium may be formed as an active layer followed by molybdenum as a barrier layer. In general, the molybdenum layer can protect the titanium layer from excessive oxidation prior to brazing and may act as a barrier material between the gold brazing material and the titanium layer. Such layers may allow for the brazing material, such as gold, to wet the insulator and form the hermetic seal. While titanium and molybdenum are mentioned, it should be understood that other metallization materials may also be employed. These may include titanium, niobium, chromium, zirconium, or vanadium as materials for the active layer with molybdenum, platinum, palladium, tantalum or tungsten as materials for the barrier layer. These layers may be formed by sputtering or other chemical vapor deposition techniques, laser or other physical vapor deposition techniques, vacuum evaporation, thick film application methods, plating, etc.

In one embodiment, the hermetically sealing material is coated with a resin. For instance, such resin may be a nonconductive resin. In one embodiment, such resin may be a thermosetting polymer. In particular, such resin may be an epoxy resin. In certain embodiments, such resin may coat the hermetically sealing material present between the insulator and the feedthrough ferrule. In one embodiment, the resin may coat the hermetically sealing material present between the insulator and the conductive terminal pins. In another embodiment, the resin may coat the hermetically sealing material present between the insulator and the RF pin, when present.

For application, the thermosetting resin may be applied in a non-cured form. For instance, such resin may be in a liquid state or semi-solid state and may be applied to coat the hermetically sealing material. Furthermore, in one embodiment, the resin may be extended to coat not only the hermetically sealing material, but also some of the insulator. In one embodiment, the resin does not extend to cover the entire area over the insulator between two adjacent conductive terminal pins.

As indicated, the EMI feedthrough filter terminal assembly includes an insulative layer between the insulator and the feedthrough filter capacitor. In addition, the conductive terminal pins may extend through the insulative layer, for instance in a non-conductive manner. In addition, the insulative layer may be in direct contact with the insulator. In one embodiment, the insulative layer includes a thermosetting polymer. For instance, the thermosetting polymer may include a polyimide.

In one embodiment, the insulative layer may be a laminated insulative layer. For instance, the laminated insulative layer may include a top layer, a middle layer, and a bottom layer opposite the top layer. The middle layer may include a conductive thermosetting polymer, such as a polyimide. Nevertheless, it should be understood that other conductive thermosetting polymers may also be employed. Meanwhile, the top layer and/or the bottom layer may comprise an adhesive layer. The adhesive layer may not necessarily be limited.

Furthermore, the EMI feedthrough filter terminal assembly may include a washer between the insulative layer and the feedthrough filter capacitor. For instance, the washer may surround the conductive terminal pin. In particular, each conductive terminal pin may include a washer surrounding the pin. The washer may be made from a conductive thermosetting polymer. For instance, the washer may be made from a polyimide. However, it should be understood that the present invention may be practiced without the aforementioned washer.

Furthermore, the EMI feedthrough filter terminal assembly may include wire bond pads. These pads may be attached by soldering, welding, brazing, thermal conductive polymer or the like. The wire bond pad can be made from any type of material known in the art. For instance, the wire bond pad may be made from materials including nickel, copper, steel and the like. The pad may also be formed from other materials such as tantalum, molybdenum, titanium, titanium alloys, rhodium, osmium, silver, silver alloys, vanadium, platinum, platinum alloys, niobium, stainless steel, tungsten, rhenium, zirconium, vanadium, ruthenium, etc. In addition, the wire bond pad may also be finished or plated. For instance, the wire bond pad may be gold plated.

Figure 2:
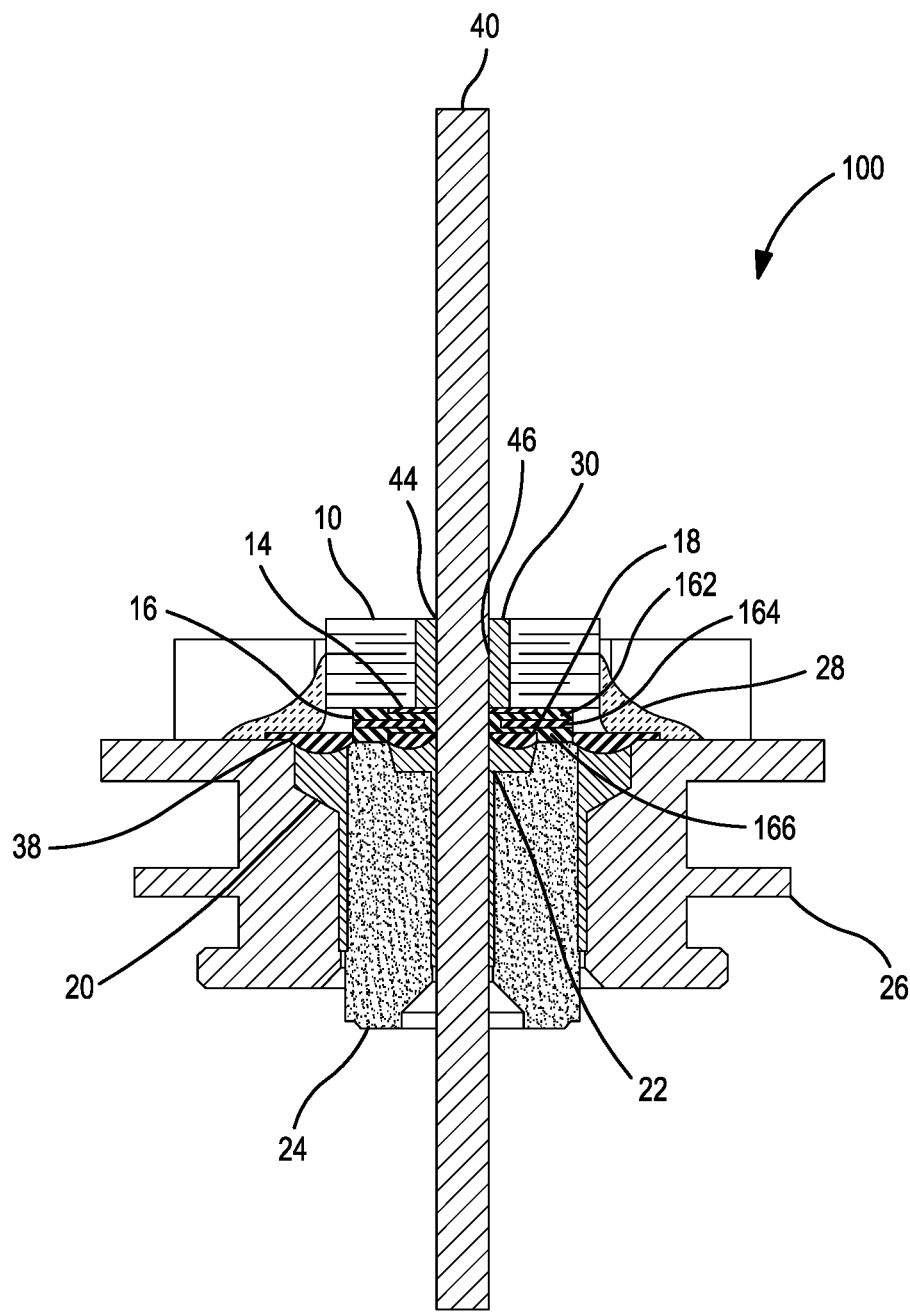
FIG. 2 illustrates a side cross-sectional view of one embodiment of a feedthrough filter assembly according to the present invention.
Figure 3:
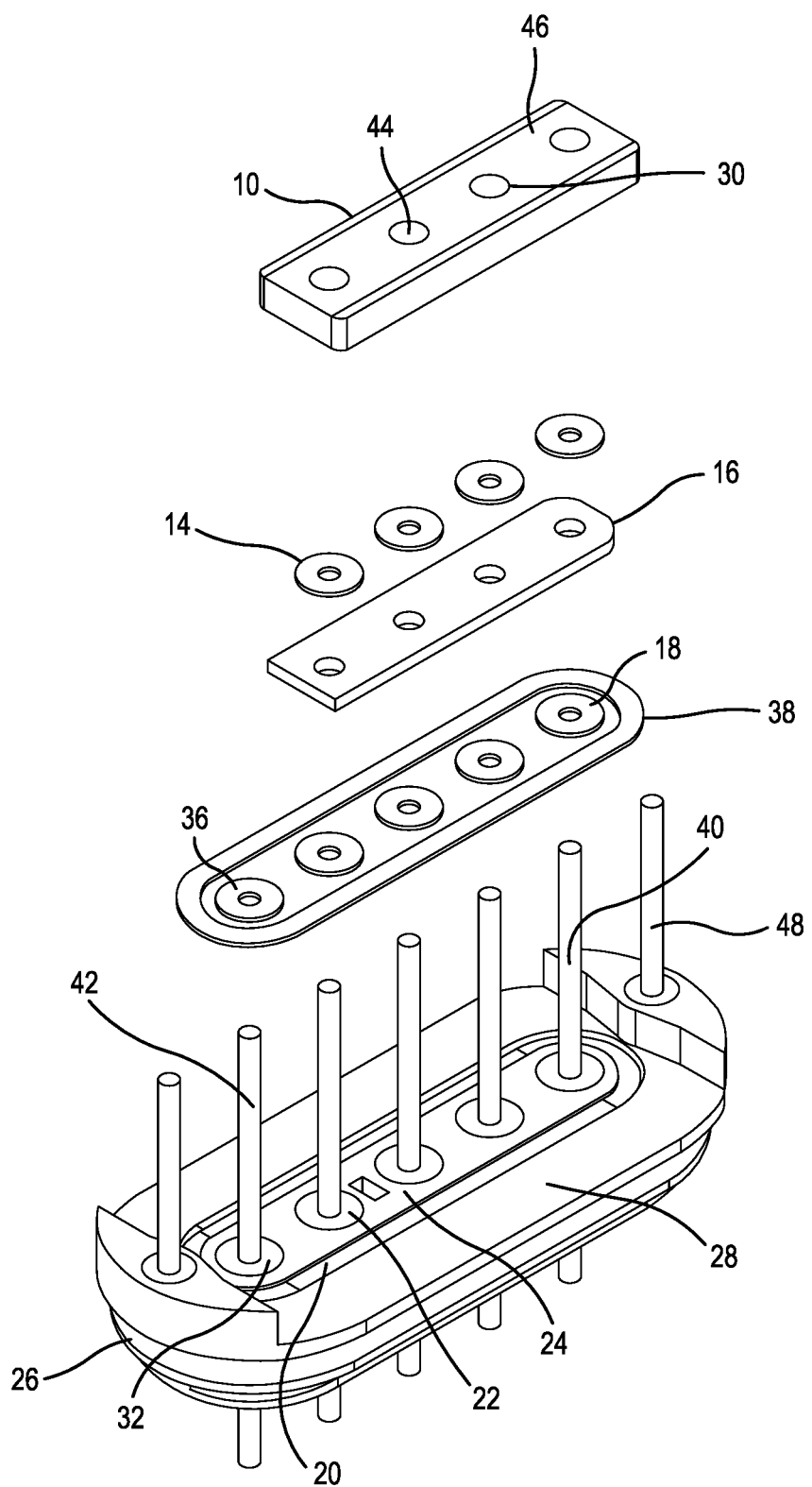
FIG. 3 illustrates an exploded view of one embodiment of a feedthrough filter assembly according to the present invention.
Figure 4:
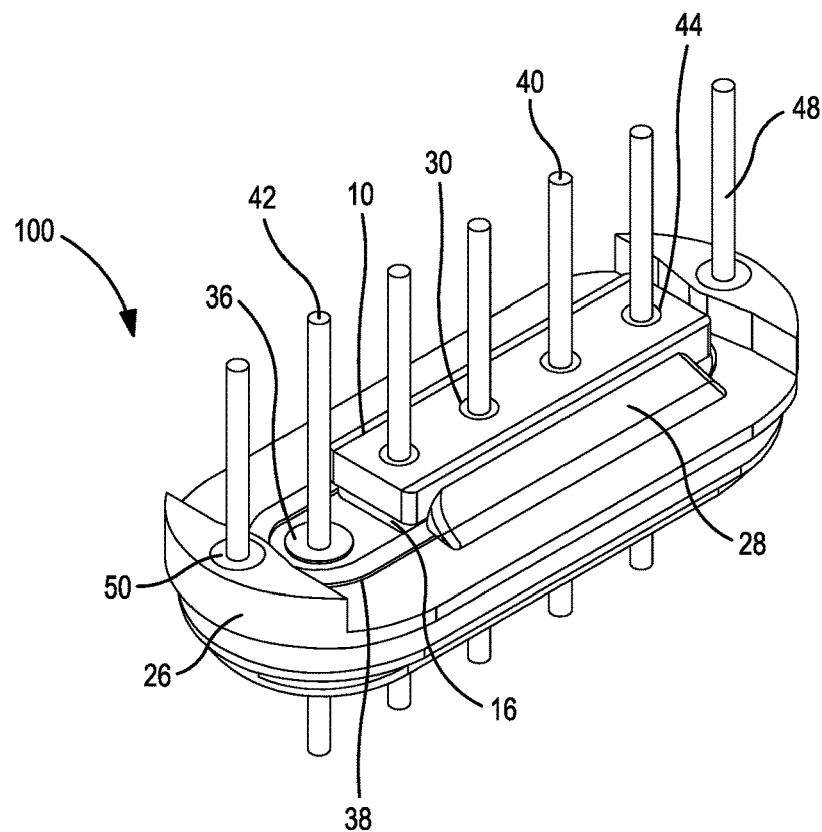
FIG. 4 illustrates a top view of one embodiment of a feedthrough filter assembly according to the present invention.
Figure 5:
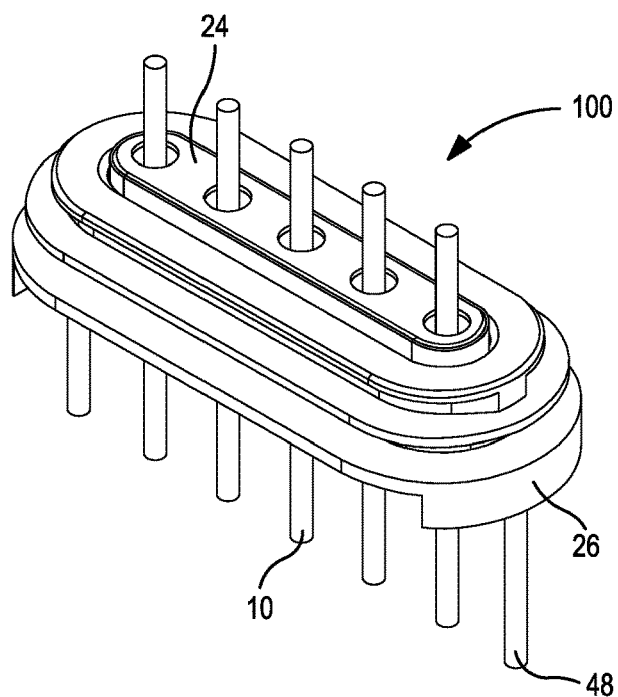
FIG. 5 illustrates a bottom view of one embodiment of a feedthrough filter assembly according to the present invention.

The EMI feedthrough filter terminal assembly can be further described according to the embodiments as illustrated in FIGS. 1-5. In the figures, an EMI feedthrough filter terminal assembly 100 is illustrated.

The EMI feedthrough filter terminal assembly 100 includes a capacitor 10, conductive terminal pins 40, an insulator 24, and a feedthrough ferrule 26. The capacitor 10 includes a passageway 44 through which the conductive terminal pin 40 extends. The inner diameter cylindrical surface 46 of passageway 44 of the capacitor 10 includes a conductive material 30 for conductively coupling the capacitor 10 to the conductive terminal pins 40. In addition, the capacitor 10 may be conductively coupled to the feedthrough ferrule 26 via a conductive joint 28. In addition, an insulative layer is positioned between the capacitor 10 and the insulator 24. A washer 14 surrounding the conductive terminal pins 40 may also be positioned between the insulative layer 16 and the capacitor 10.

As also illustrated in the figures, a hermetic seal is formed. The hermetic seal can be formed using any method known in the art. For instance, the hermetic seal may include a hermetically sealing material 20 between the insulator 24 and the feedthrough ferrule 26. The hermetic seal may also include a hermetically sealing material 22 between the insulator 24 and the conductive terminal pins 40. When the RF pin 42 is present, the hermetic seal may also include a hermetically sealing material 32 between the insulator 24 and the RF pin 42. When other pins 48 are present, the hermetically sealing material 50 may be present between the feedthrough ferrule 26 and the pins 48.

As illustrated in the figures, the EMI feedthrough filter terminal assembly 100 includes a resin coating 38, 18, 36 over the hermetically sealing material 20, 22, 32, respectively. For instance, a resin coating 38 may be present over the hermetically sealing material 20 between the insulator 24 and the feedthrough ferrule 26. In such instance, the resin coating 38 may not be covered by any other material or sandwiched.

Also, a resin coating 18 may be present over the hermetically sealing material 22 between the insulator 24 and the conductive terminal pins 40. In such instance, the resin coating 18 may not be covered by another material. For instance, the resin coating 18 may be covered by the insulative layer 16. When the RF pin 42 is present, a resin coating 36 may be present over the hermetically sealing material 32 between the insulator 24 and the RF pin 42. In such instance, the resin coating 36 may not be covered by any other material or sandwiched.

As illustrated in the figures, the EMI feedthrough filter terminal assembly 100 includes four conductive terminal pins 40. In addition, the EMI feedthrough filter terminal assembly 100 includes an RF pin 42. However, it should be understood that the EMI feedthrough filter terminal assembly 100 may include more or less conductive terminal pins. In addition, the EMI feedthrough filter terminal assembly 100 may or may not include an RF pin 42.

While not expressly stated herein, it should be understood that the EMI feedthrough filter terminal assembly can be manufactured according to any method generally known in the art. For instance, the formation of the hermetic seal, in particular the use of gold brazing, can be performed using any method known in the art. In this regard, the formation of the hermetic seal with the conductive terminal pins extending through the capacitor, insulative material, feedthrough ferrule, and insulator can be conducted using any method known in the art. In addition, when desired to cure the polyimide, such curing may be done using any method known in the art, such as thermal curing.

The EMI feedthrough filter terminal assemblies can be employed in various applications. For instance, the EMI feedthrough filter terminal assemblies can be employed in those applications where it may be desirable to decouple and shield undesirable electromagnetic interference signals from the device. For instance, these may include implantable medical devices such as cardiac pacemakers, cardioverter defibrillators, neuro-stimulators, internal drug pumps, cochlear implants and other medical implant applications. In general, the housing for these materials include a biocompatible metal which is electrically and mechanically coupled to the hermetic terminal pin assembly which is electrically coupled to the feedthrough filter capacitor. As a result, the filter capacitor and terminal pin assembly prevents entrance of interference signals to the interior of the device.

Nevertheless, the EMI feedthrough filter terminal assemblies disclosed herein may also be employed for other EMI filter applications, such as military or space electronic modules, where it is desirable to preclude the entry of EMI into a hermetically sealed housing containing sensitive electronic circuitry.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An EMI feedthrough filter terminal assembly comprising:
    a feedthrough filter capacitor having
        a plurality of first electrode layers and a plurality of second electrode layers, and
        a first passageway therethrough having a first termination surface conductively coupling the plurality of first electrode layers,
    at least one conductive terminal pin extending through the passageway in conductive relation with the plurality of first electrode layers,
    a feedthrough ferrule,
    an insulator fixed to the feedthrough ferrule for conductively isolating the conductive terminal pin from the feedthrough ferrule,
    a first hermetically sealing material between the insulator and the feedthrough ferrule and a second hermetically sealing material between the insulator and the conductive terminal pin, and
    a first resin coating over the entire first hermetically sealing material and a second resin coating over the entire second hermetically sealing material.

2. The EMI feedthrough filter terminal assembly of claim 1, wherein the first and second hermetically sealing material comprise gold brazing.

3. The EMI feedthrough filter terminal assembly of claim 1, wherein the first and second resin coatings comprise an epoxy coating.

4. The EMI feedthrough filter terminal assembly of claim 1, further comprising an insulative layer between the insulator and the feedthrough filter capacitor.

5. The EMI feedthrough filter terminal assembly of claim 4, wherein the insulative layer includes a polyimide layer.

6. The EMI feedthrough filter terminal assembly of claim 4, wherein the insulative layer includes a laminated insulative layer including a top layer, a middle layer, and a bottom layer opposite the top layer, wherein the middle layer comprises a polyimide layer.

7. The EMI feedthrough filter terminal assembly of claim 6, wherein the top layer and the bottom layer comprise adhesive layers.

8. The EMI feedthrough filter terminal assembly of claim 4, further comprising a washer between the insulative layer and the feedthrough filter capacitor wherein the washer surrounds the conductive terminal pin.

9. The EMI feedthrough filter terminal assembly of claim 8, wherein the washer comprises a polyimide.

10. The EMI feedthrough filter terminal assembly of claim 1, wherein the first termination surface comprises a conductive polyimide.

11. The EMI feedthrough filter terminal assembly of claim 1, wherein the feedthrough filter capacitor comprises a second termination surface conductively coupling the plurality of second electrode layers.

12. The EMI feedthrough filter terminal assembly of claim 11, wherein the second termination surface is conductively coupled to the feedthrough ferrule via a conductive polyimide.

13. The EMI feedthrough filter terminal assembly of claim 1, wherein the feedthrough filter capacitor is internally grounded via a ground pin.

14. The EMI feedthrough filter terminal assembly of claim 1, wherein the assembly includes four conductive terminal pins.

15. The EMI feedthrough filter terminal assembly of claim 1, wherein the assembly further comprises an RF pin.

16. An EMI feedthrough filter terminal assembly comprising:
    a feedthrough filter capacitor having
        a plurality of first electrode layers and a plurality of second electrode layers, and
        a first passageway therethrough having a first termination surface conductively coupling the plurality of first electrode layers,
    at least one conductive terminal pin extending through the passageway in conductive relation with the plurality of first electrode layers,
    a feedthrough ferrule,
    an insulator fixed to the feedthrough ferrule for conductively isolating the conductive terminal pin from the feedthrough ferrule,
    an insulative layer between the insulator and the feedthrough filter capacitor wherein the insulative layer includes a laminated insulative layer including a top layer, a middle layer, and a bottom layer opposite the top layer and wherein the middle layer comprises a polyimide layer,
    a hermetically sealing material between the insulator and the feedthrough ferrule and between the insulator and the at least one conductive terminal pin, and
    a resin coating over the hermetically sealing material.

17. An EMI feedthrough filter terminal assembly comprising:
    a feedthrough filter capacitor having
        a plurality of first electrode layers and a plurality of second electrode layers, and
        a first passageway therethrough having a first termination surface conductively coupling the plurality of first electrode layers,
    at least one conductive terminal pin extending through the passageway in conductive relation with the plurality of first electrode layers,
    a feedthrough ferrule,
    an insulator fixed to the feedthrough ferrule for conductively isolating the conductive terminal pin from the feedthrough ferrule,
    an insulative layer between the insulator and the feedthrough filter capacitor wherein the insulative layer includes a laminated insulative layer including a top layer, a middle layer, and a bottom layer opposite the top layer,
    a hermetically sealing material between the insulator and the feedthrough ferrule, and
    a resin coating over the hermetically sealing material.

* * * * *